United States Patent [19]

Diamantoglou et al.

[11] Patent Number: 4,543,409
[45] Date of Patent: Sep. 24, 1985

[54] WATER-INSOLUBLE FIBERS OF CELLULOSE ACETATE, CELLULOSE PROPIONATE AND CELLULOSE BUTYRATE WITH AN EXTREMELY HIGH ABSORPTIVE CAPACITY FOR WATER AND PHYSIOLOGICAL LIQUIDS

[75] Inventors: Michael Diamantoglou, Erlenbach; Alexander Brandner, Steyrermühl; Gerhard Meyer, Obernburg, all of Fed. Rep. of Germany

[73] Assignee: AKZO NV, Arnhem, Netherlands

[21] Appl. No.: 560,285

[22] Filed: Dec. 12, 1983

[30] Foreign Application Priority Data

Dec. 15, 1982 [DE] Fed. Rep. of Germany ....... 3246417

[51] Int. Cl.[4] .......................... C08B 3/08; C08B 3/06; D02G 3/00; D01F 2/00
[52] U.S. Cl. ....................................... 536/68; 536/69; 428/364; 264/187
[58] Field of Search ................ 428/364, 359; 264/200, 264/187, 203; 536/68, 69

[56] References Cited

U.S. PATENT DOCUMENTS

| | | | |
|---|---|---|---|
| 1,866,532 | 7/1932 | Haskins | 536/68 |
| 1,908,499 | 5/1933 | Webber et al. | 536/68 |
| 2,072,102 | 3/1937 | Dreyfus | 264/200 |
| 2,702,230 | 2/1955 | Olmer | 264/200 |
| 4,302,252 | 11/1981 | Turbak et al. | 264/187 |
| 4,352,770 | 10/1982 | Turbak et al. | 264/187 |

*Primary Examiner*—Marion E. McCamish
*Assistant Examiner*—Beverly K. Johnson
*Attorney, Agent, or Firm*—Michael J. Striker

[57] ABSTRACT

The invention refers to water-insoluble fibers of cellulose acetate cellulose propionate and cellulose butyrate with an extremely high absorptive capacity for water and physiological liquids and to a process for their preparation.

2 Claims, 1 Drawing Figure

WATER-INSOLUBLE FIBERS OF CELLULOSE ACETATE, CELLULOSE PROPIONATE AND CELLULOSE BUTYRATE WITH AN EXTREMELY HIGH ABSORPTIVE CAPACITY FOR WATER AND PHYSIOLOGICAL LIQUIDS

BACKGROUND OF THE INVENTION

As heretofore, a need exists for fiber goods with improved absorbency in the field of sanitary products, medicine, household articles, clothing and technical applications. Thereby, the more and more stringent physiological requirements, in particular in the areas of sanitary products and medicine, limit the possibilities of a selection among hydrophilic fiber modifications to a considerable extent. Viscose fibers modified to be hydrophilic are known under the tradename Viscosorb (cf. Lenzinger Berichte, Issue 51, 1981, page 34ff). Even though they meet the requirements of Deutsches Arzneibuch (German Pharmacopoeia, hereinafter "DAB") and Europaesches Arzneibuch (European Pharmocapoeia, hereafter "EAB") to some extent, their water retentivity still is in need of improvement.

Cellulose acetates, in the form of amorphous products and fibers, have been known for a long time. Acetate fibers are prepared with an acetic acid content of about 53 to 55%, which corresponds to a degree of esterification of 2.3. At a degree of esterification of 1.2 to 3, the known cellulose acetates are water-insoluble, but at the lower degrees of esterification of 0.6 to 0.9 they are soluble in water (cf. Ullmann, Vol. 9, 4th Edition, 1975, table 4, page 233 and page 238) and Ott et al *Cellulose and Cellulose Derivatives,* 2nd Ed., Part III, Interscience Publishers, Inc., 1955, pages 1076-7 and 1460. The known cellulose acetates with degrees of esterification in the range of 1.2 to 1.8 are also soluble in 2 methoxyethanol (Ullman, ibid.).

Previously, cellulose esters with low acetic acid content, such as involved here, were obtained through hydrolysis via the triester stage. The excess of anhydride was destroyed by the addition of water and a certain number of acetyl groups was split off again by the addition of more sulfuric acid. The consumption of acetic anhydride and sulfuric acid was correspondingly high (Ullmann, Vol. 9, 1975, pages 228 and 230).

It is the goal of the present invention to make available new water-insoluble fibers with an improved absorbency for water and physiological liquids, which, in addition, also meet the increased physiological demands in the areas of sanitary products and medicine.

The objects of the invention are water-insoluble fibers of cellulose acetate, cellulose propionate and cellulose butyrate, with an extremely high absorptive capacity for water and physiological liquids, which are characterized by the fact that they exhibit (a) in the sequence as mentioned, a degree of esterification of 0.1 to 1.5, 0.1 to 0.95 and 0.15 to 0.8.

(b) an average degree of polymerization from 300 to 700;

(c) a fiber strength in the conditioned state of 6 to 20 cN/tex;

(d) an elongation in the conditioned state of 6 to 20%;

(e) a water retentivity of 200 to 750%; and (f) a wicking capacity for water of 8 to 18 cm/g of fiber.

DESCRIPTION OF THE DRAWING

The FIGURE shows the water retentivity (WR) and retentivity for synthetic urine (SUR) of the fibers pursuant to the invention relative to the degree of esterification or degree of substitution.

DETAILED DESCRIPTION OF THE INVENTION

Figure 1:
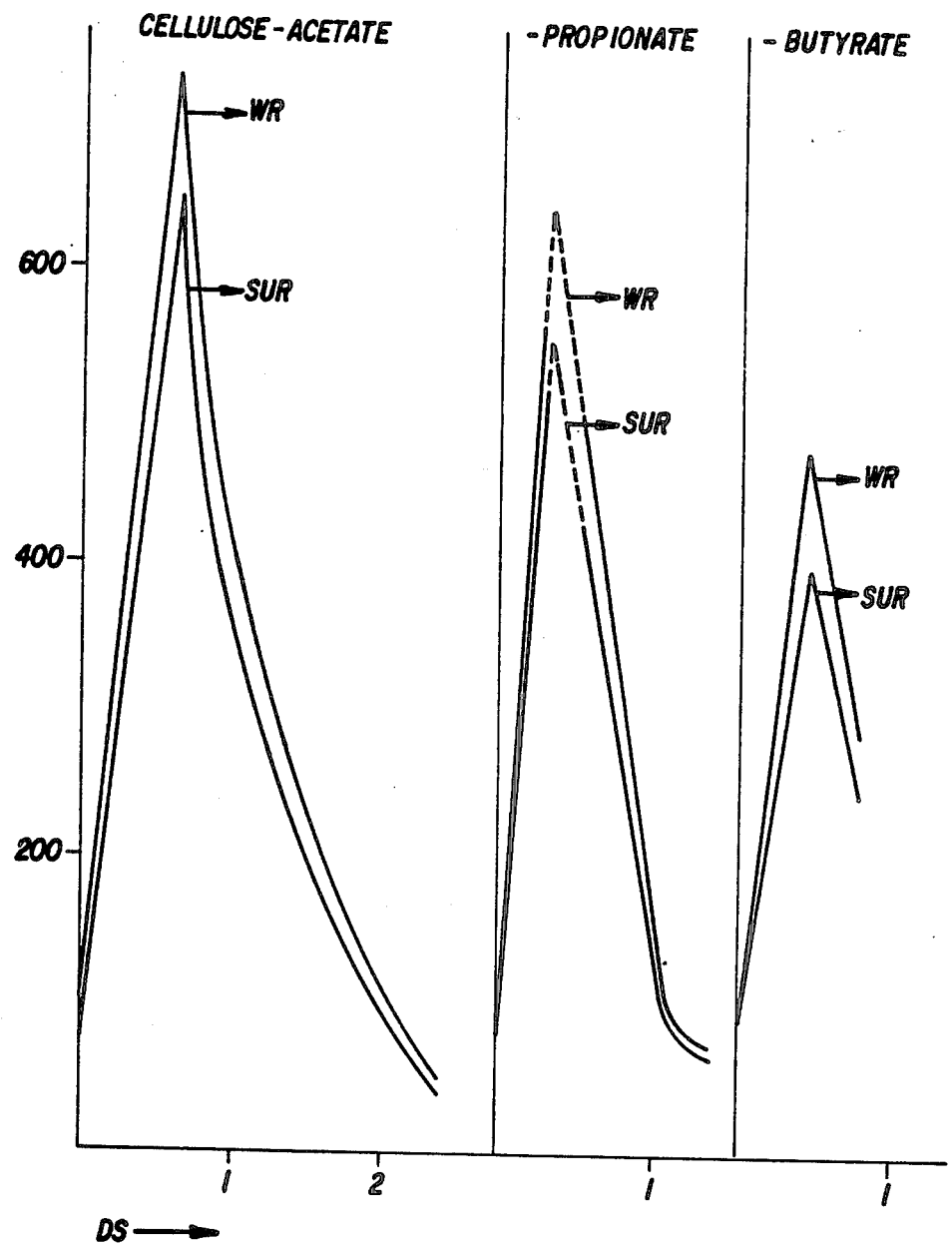

It was surprising to us that fibers made according to the invention exhibit an enormous increase in absorptive capacity for water and physiological liquids within very narrowly defined ranges of the degree of esterification.

According to DIN 53 814, the water retentivity is a measure for the water retained in the individual fibers after abundant immersion in water, followed by defined centrifuging. The same applies to the retentivity for synthetic urine, which was measured according to the same test procedure.

In the case of the cellulose acetate fibers pursuant to the invention, the curve of the WR data rises steeply at very low degrees of esterification (the same applies to the corresponding SUR data) and reaches the noteworthy WR value of 200% at a degree of esterification (DS) of 0.13. The water retentivity then passes through a maximum of 720% at a degree of esterification of 0.70, whereupon it continuously drops steeply with increasing degrees of esterification. The same relationships also apply to the cellulose propionate and cellulose butyrate fibers pursuant to the invention, with the proviso that, with increasing chain length of the monocarboxylic acid, the attainable WR and SUR maxima become a little lower and, like the upper limit of the recommended range of the degree of esterification, are shifted towards lower values. The FIGURE shows, furthermore, that in each case the differences between the corresponding WR and SUR data are small, which expands the range of application of the fibers pursuant to the invention in an advantageous manner.

The curves show that especially high WR and SUR data are obtained when the degree of esterification of the cellulose acetate fibers is located within a range of 0.5 to 0.8, that of the cellulose propionate fibers within a range of 0.25 to 0.55 and that of the cellulose butyrate fibers within a range of the degree of esterification of 0.35 to 0.55. These data are applicable to the average degree of polymerization (DP) of the fibers from 300 to 700, and fibers having a DP within that range have fiber strengths and fiber elongations in the ranges indicated above, which are more than satisfactory for the specific purposes.

Fibers of cellulose acetate, cellulose propionate and cellulose butyrate which exhibit the above-mentioned preferred ranges of degree of esterification are the preferred form of the invention. The preferred fibers exhibit the following properties:

a. a fiber strength in the conditioned state of 10 to 16 cN/tex;

b. an elongation in the conditioned state of 8 to 12%; and c. a water retentivity of 400% to 720%.

It was surprising, also, to discover that cellulose acetate fibers obtained by the invention were absolutely water-insoluble in the preferred range of the degree of esterification of 0.5 to 0.8. As already explained above, cellulose acetate fibers of the state of the art, prepared according to other processes, are water-soluble in this range, so that they could not at all be considered for the end-use areas intended here.

It was also observed that the fibers of the invention are insoluble in 2-methoxyethanol, whereas, as pointed out above, known fibers in this D.S. range are soluble.

In addition to the extremely high absorptive capacity for water and physiological liquids, the water-insoluble fibers pursuant to the invention also exhibit an increased wicking capacity for water. The latter is measured by means of the demand-wettability test (cf. Bernard M. Lichstein, INDA, 2nd Annula Symposium on Non-Woven Product Development, Mar. 5–6, 1974, Washington, D.C.) which, being a highly application-oriented test, indicates the average wicking rate and wicking capacity of a wicking material, even under a certain surface pressure, with the measuring liquid itself not exerting any pressure on the specimen. Since the fibers pursuant to the invention have a fiber pH value of less than 7 and do not contain any water-soluble constituents, they meet the demands of the DAB and EAB. Consequently, they can also be used where, in order to solve the absorption problem, a direct contact between fibers and open wounds or sensitive mucous membranes is required, i.e., in the form of tampons, swabs, absorptive dressings, etc. Additional purposes that can be mentioned are, e.g., the manufacture of diapers, wiping cloths, vapor filters and telephone cable insulations.

The invention also refers to a process for the manufacture of the water-insoluble cellulose acetate, cellulose propionate and cellulose butyrate fibers under discussion.

The process for making the fibers comprises:
 a. preparing a solution of activated cellulose by dissolving from 5 to 13% by weight of activated cellulose, having an average degree of polymerization of 400 to 800, and 3 to 10% by weight of LiCl in dimethyl acetamide or 1-methyl-2-pyrrolidone at a temperature of 20° to 80° C.
 b. reacting the activated cellulose solution with an acid anhydride selected from the group consisting of acetic anhydride, propionic anhydride and butyric anhydride in a molar ratio of 1:0.5 to 1:4, at 20° to 50° C., in the presence of any well-known esterification catalyst, until the desired degree of esterification, mentioned above, is reached, and
 c. Spinning the cellulose ester solutions obtained into a coagulant in accordance with conventional wet spinning process techniques.

The solutions of activated cellulose in dimethyl acetamide or 1-methyl-2-pyrrolidone, which contain LiCl, can be prepared as disclosed in U.S. Pat. Nos. 4,302,252 and 4,352,770. This literature describes several process variants for the activation of the cellulose and the preparation of the mentioned solutions and is hereby incorporated by reference.

The process for preparing fibers pursuant to the invention is characterized by the fact that the organic cellulose solutions are reacted only until the above-defined low and narrowly limited degrees of esterification are reached. Thereby, one gets not only a savings of acetic anhydride and catalysts but, surprisingly, one also obtains, in particular, substances of an entirely different and, heretofore, unknown quality. It has already been pointed out that, according to the preparation methods of the state of the art, the preferred cellulose acetate fibers pursuant to the invention, with a degree of esterification of 0.6 to 0.9, are water-soluble and consequently exhibit entirely different physical characteristics. The same conclusion is drawn with respect to cellulose acetate fibers with a D.S. of 1.2 to 1.5 of the invention in view of their insolubility in 2-methoxyethanol compared to the solubility of known cellulose acetate fibers in 2-methoxyethanol. Due to the different preparation process and the targeted selection of narrowly limited ranges of a low degree of esterification, the cellulose esters pursuant to the invention, compared with those of the state of the art, obviously have a different chemical constitution. Many esterification catalysts are known and are suitable for the esterification reaction, e.g., acids, such as methanesulfonic acid, perchloric acid, formic acid and sulfuric acid, or acid chlorides, such as acetyl chloride and propionyl chloride. These acid esterification catalysts are used in quantities of about 2 to 10% by weight based on the amount of acid anhydride.

Also, basic esterification catalysts are well suited for the esterification reactions in question, especially since they counteract a decomposition of the cellulose. As examples of such compounds one can mention: 4,N,N-dimethylaminopyridine, collidine, pyridine and triethylamine. Such basic esterification catalysts are used in equimolar quantities based on the acid anhydride in order to bind the acid liberated during the reaction. Basic salts of monocarboxylic acids, such as sodium acetate, potassium acetate, sodium propionate, potassium propionate, sodium butyrate and potassium butyrate are likewise suitable esterification catalysts. In general, these salts are used in quantities of 6 to 20% by weight, preferably 8 to 13% by weight, based on the acid anhydride.

Especially advantageous cellulose ester fibers are obtained when a solution of activated cellulose in dimethyl acetamide containing 8 to 12% by weight of activated cellulose having an average degree of polymerization of 600 to 800 is reacted, at a temperature of 20° to 30° C., with the selected acid anhydride followed by wet-spinning of the reaction product.

Because of the low temperatures that are used, decomposition of the cellulose can largely be avoided; thus the combination of the higher molecular weights of the cellulose and the higher solution concentrations contribute to improved mechanical characteristics of the spun fibers.

The cellulose ester solutions pursuant to the invention are spun according to conventional wet spinning methods and with conventional equipment used for the purpose. In wet spinning, the appropriately prepared cellulose ester solution is extruded through nozzles with fine borings into a suitable coagulating bath, e.g., a water bath held at 20° to 60° C. Other suitable coagulants are mixtures of water and water-soluble organic solvents, such as alcohols, ketones, ether, or the solvent used for the dissolving of the cellulose. Development of maximal fiber characteristics is aided by passing the fibers, combined into a tow, through a series of baths containing aqueous or organic solvents and, if required, inorganic salts, in order to remove residues of the solvents used and of LiCl. The aftertreatment can simultaneously be combined with stretching, which permits a setting of the mechanical fiber properties that are desired. The stretch ratio can be varied from 1:1 to 3:1.

The invention is further illustrated by the following examples:

EXAMPLE 1

16.2 g (0.1 mol) of cellulose (DP: 700, measured in cupriethylene diamine solvent) were suspended in 278.4 g (3.2 mol) of industrial-grade dimethyl acetamide (DMAC) in a 1 lit. three-necked flask and activated for 30 min. at 155° C. After cooling to 100° C., 29 g (0.68 mol) LiCl were added, whereby the temperature rises by 5° to 10° C.; this is followed by cooling to room temperature (RT always 20° to 25° C.). A gel-like cellulose solution was obtained after 2 to 3 hours of stirring at room temperature. Stirring is continued overnight. This resulted in a clear, viscous cellulose solution, which was acetylated for 20 hours at room temperature using a mixture of 12.24 g (0.12 mol) of acetic anhydride and 1.18 g (0.015 mol) of acetyl chloride. The reaction mixture is deaerated, spun through a viscose spinneret (36/90) into a precipitating bath of water/alcohol (30/70), washed and dried.

The cellulose acetate fibers obtained in this manner exhibit the following characteristics:
Degree of esterification (DS): 0.60
Degree of polymerization (DP): 570
Fiber strength, conditioned: 12.4 cN/tex
Fiber elongation, conditioned: 8.9%
Water retentivity (WR): 640%
Synth. urine retentivity (SUR): 560%

EXAMPLES 2 TO 20

The cellulose acetates of Examples 2-20 were prepared and, where indicated, were spun according to the same process as indicated in Example 1.

a. Examples 2 to 7, listed in Table 1 for the preparation of cellulose acetate fibers, show the influence of variable quantities of acetic anhydride. Kind and quantity of catalyst, reaction temperature and reaction time were kept constant: reaction temperature: room temperature (RT); reaction time: 20 hours; catalyst: 2% by weight of acetyl chloride, referred to the acid anhydride.

TABLE 1
(Cellulose Acetate)
Esterification of Cellulose with Varying Acetic Anhydride Quantities

| Example | Molar Ratio Cellulose:Acid Anhydride | DS | DP | WR (%) | SUR (%) | Fiber Strength Cond. (cN/tex) | Fiber Elong. Cond. (%) |
|---|---|---|---|---|---|---|---|
| 2 | 1:1.0 | 0.13 | 650 | 270 | 235 | 19.6 | 12.0 |
| 3 | 1:1.5 | 0.23 | 610 | 310 | 270 | 16.3 | 11.4 |
| 4 | 1:2.0 | 0.57 | 560 | 635 | 540 | 12.1 | 8.5 |
| 5 | 1:2.5 | 0.82 | 520 | 545 | 460 | 12.7 | 9.7 |
| 6 | 1:3.0 | 0.89 | 525 | 470 | 395 | 13.5 | 10.6 |
| 7 | 1:4.0 | 1.50 | 510 | 240 | 205 | 14.8 | 11.3 | b. Examples 3 and 8 to 12, listed in Table 2, show the dependence of the degree of esterification upon different acid catalysts. In these examples the reaction temperature and time, catalyst quantity and molar ratio of cellulose to acid anhydride were held constant: reaction temperature: RT; reaction time: 20 hours; molar ratio of cellulose: acid anhydride=1:1.5; quantity of catalyst: 2% by wt. based on acid anhydride. The fiber of Example 7 was insoluble in 2-methoxyethanol.

TABLE 2
(Cellulose Acetate)
Dependence of the Degree of Esterification Upon The Type of Catalyst

| Example | Catalyst | DS |
|---|---|---|
| 3 | $CH_3COCl$ | 0.23 |
| 8 | $CH_3SO_3H$ | 0.38 |
| 9 | $HClO_4$ | 0.24 |
| 10 | $H_2SO_4$ | 0.13 |
| 11 | HCOOH | 0.15 |
| 12 | none | 0.11 | c. Using acetyl chloride as the catalyst the influence of increasing catalyst concentrations is shown by Examples 3, 13 and 14, with the results listed in Table 3. In these experiments, the work was performed with reaction temperature, reaction time and the molar ratio of cellulose to acid anhydride as constant parameters as follows: reaction temperature: RT; reaction time: 20 hours; molar ratio of cellulose:acid anhydride=1:1.5.

TABLE 3
(Cellulose Acetate)
Dependence of the Degree of Esterification Upon the Catalyst Quantity

| Example | Catalyst and Quantity (Basis:Acid Anhydride) | | DS |
|---|---|---|---|
| 3 | acetyl chloride | 2% by weight | 0.23 |
| 13 | acetyl chloride | 5% by weight | 0.58 |
| 14 | acetyl chloride | 10% by weight | 0.78 | d. Examples 3 and 15-16, the results of which are listed in Table 4, show the influence of variable reaction times. The catalyst used was 2% by weight of acetyl chloride (basis: acid anhydride), and the reaction temperature and the molar ratio of cellulose to acid anhydride were also held constant. Molar ratio of cellulose:acid anhydride=1:1.5; reaction temperature: RT.

TABLE 4
(Cellulose Acetate)
Dependence of The Degree of Esterification Upon The Reaction Time

| Example | Reaction Time | DS |
|---|---|---|
| 3 | 20 | 0.23 |
| 15 | 6 | 0.20 |
| 16 | 48 | 0.45 | e. Table 5 shows the influence of a variable reaction temperature. Kind and quantity of catalyst, the reaction time, and the molar ratio of cellulose to acid anhydride were kept constant in Examples 15, 17 and 18, as follows: molar ratio of cellulose:acid anhydride=1:1.5; catalyst: 2% by weight acetyl chloride, based on the acid anhydride; reaction time: 6 hours TABLE 5
(Cellulose Acetate)
Dependance of the Degree of Esterification Upon The Reaction Temperature

| Example | Reaction Temperature (°C.) | DS |
|---|---|---|
| 15 | RT | 0.20 |
| 17 | 40-50 | 0.37 |
| 18 | 60-70 | 0.48 | f. The degree of esterification also depends considerably upon the purity of the solvent used, as is demonstrated in Table 6, using dimethyl acetamide (DMAC)

as the solvent. In Examples 3, 13, 19 and 20, the parameters of reaction temperature and time, catalyst and molar ratio of cellulose to acid anhydride were kept constant: reaction temperature: RT; reaction time: 20 hours; molar ratio of cellulose:acid anhydride = 1:1.5.

TABLE 6

(Cellulose Acetate)
Dependance of the Degree of Esterification
Upon The Purity of the Solvent

| Example | Catalyst and Quantity (Basis:Acid Anhydride) | Purity of Solvent | DS |
|---|---|---|---|
| 3 | CH$_3$COCl 2% by weight | industr. grade DMAc | 0.23 |
| 13 | CH$_3$COCl 5% by weight | industr. grade DMAc | 0.58 |
| 19 | CH$_3$COCl 2% by weight | analysis grade DMAc | 0.80 |
| 20 | CH$_3$COCl 5% by weight | analysis grade DMAc | 0.98 |

EXAMPLES 21 TO 28

In Examples 21 to 28, cellulose acetates were prepared by the same procedure as Example 1, using different basic catalysts and varying the molar ratios of cellulose to acid anhydride. Reaction temperature and time were kept constant: reaction temperature: RT; reaction time: 20 hours. As in Example 1, the resulting cellulose acetates can be spun easily. The results are listed in Table 7. The fiber of Example 28 was insoluble in 2-methoxyethanol.

TABLE 7

(Cellulose Acetate)
Esterification of Cellulose With Acetic
Anhydride In The Presence Of A Tertiary Amine

| Example | Molar Ratio Cellulose:Acid Anhydride | Tertiary Amine | DS | DP |
|---|---|---|---|---|
| 21 | 1:0.25 | 0.25 mol 4-N,N—dimethyl-aminopyridine | 0.19 | 645 |
| 22 | 1:0.50 | 0.50 mol 4-N,N—dimethyl-aminopyridine | 0.42 | 625 |
| 23 | 1:1.00 | 1.00 mol 4-N,N—dimethyl-aminopyridine | 0.69 | 580 |
| 24 | 1:1.50 | 1.50 mol 4-N,N—dimethyl-aminopyridine | 1.11 | 545 |
| 25 | 1:2.00 | 2.00 mol 4-N,N—dimethyl-aminopyridine | 1.52 | — |
| 26 | 1:1.50 | 1.50 mol collidine | 0.54 | 317 |
| 27 | 1:1.50 | 1.50 mol pyridine | 0.87 | 316 |
| 28 | 1:1.50 | 1.50 mol triethylamine | 1.20 | — |

EXAMPLES 29 TO 33

In Examples 29 to 33, cellulose propionates were prepared on the basis of the procedure of Example 1 and the reaction conditions listed in Table 8 and then spun into fibers. As esterification catalyst, use was made of a constant quantity of propionyl chloride. The molar ratio of cellulose to acid anhydride was varied, but the reaction temperature and reaction time were kept constant. Reaction temperature: RT; reaction time: 20 hours; catalyst: 2% by weight of propionyl chloride, referred to the acid anhydride. The fibers of Examples 32 and 33 were insoluble in 2-methoxyethanol.

TABLE 8

(Cellulose Propionate)
Esterification of Cellulose With Varying
Propionic Anhydride Quantities

| Example | Molar Ratio Cellulose:Acid Anhydride | DS | WR (%) | SUR (%) | Fiber Strength Conditioned (cN/tex) | Fiber Elongation Cond. (%) |
|---|---|---|---|---|---|---|
| 29 | 1 1.00 | 0.26 | 390 | 355 | 12.6 | 12.1 |
| 30 | 1 1.50 | 0.32 | 570 | 520 | 10.5 | 8.3 |
| 31 | 1 2.00 | 0.56 | 505 | 420 | — | — |
| 32 | 1 3.00 | 1.10 | 110 | 100 | 13.5 | 9.8 |
| 33 | 1 4.00 | 1.37 | 75 | 70 | 11.1 | 10.3 |

EXAMPLES 30 TO 36

Using the procedure of Example 1, Examples 30 to 36 indicate the dependence of the degree of esterification upon the kind and quantity of two acid esterification catalysts, which exists in the preparation of cellulose propionates. Thereby, the reaction temperature, reaction time and the molar ratio of cellulose to acid anhydride were kept constant. reaction temperature: RT; reaction time: 20 hours; molar ratio of cellulose:acid anhydride = 1:1.5

TABLE 9

(Cellulose Propionate)
Dependence of The Degree of Esterification Upon
The Kind and Quantity of The Catalyst

| Example | Catalyst (Basis:Acid Anhydride) | | DS |
|---|---|---|---|
| 30 | CH$_3$CH$_2$COCl | 2% by weight | 0.32 |
| 34 | CH$_3$CH$_2$COCl | 5% by weight | 0.73 |
| 35 | CH$_3$SO$_3$H | 2% by weight | 0.55 |
| 36 | CH$_3$SO$_3$H | 5% by weight | 0.76 |

EXAMPLES 37 TO 40

In Examples 37 to 40, cellulose butyrates were prepared following the procedure of Example 1 and then wet-spun into fibers. As the esterification catalyst, 2% of weight based on the acid anhydride of butyryl chloride was used in each example. The molar ratio of cellulose to acid anhydride was varied as listed in Table 10, while the reaction temperature and reaction time were kept constant: reaction temperature: RT; reaction time: 20 hours.

TABLE 10

(Cellulose Butyrate)
Esterification of Cellulose With Varying
Quantities of Butyric Anhydride

| Example | Molar Ratio Cellulose:Acid Anhydride | DS | WR (%) | SUR (%) | Fiber Strength Conditioned (cN/tex) | Fiber Elongation Cond. (%) |
|---|---|---|---|---|---|---|
| 37 | 1:1.00 | 0.32 | 275 | 245 | 12.4 | 9 |
| 38 | 1:1.25 | 0.44 | 475 | 390 | — | — |
| 39 | 1:1.50 | 0.50 | 460 | 385 | — | — |
| 40 | 1:1.75 | 0.80 | 285 | 245 | — | — |

EXAMPLE 41

16.2 g (0.1 mol) of cellulose were suspended in 278.4 g (3.2 mol) of industrial grade dimethyl acetamide and activated for 30 min. at 155° C. After cooling to 100° C., 29 g (0.68 mol) of LiCl were added. This is followed by cooling to room temperature and stirring overnight. To the clear, viscous solution, 1 g (0.01 mol) of potassium acetate (catalyst) and 12.24 g (0.12 mol) of acetic anhydride were added. To complete the reaction, stirring was continued for 6 hours at 80° C., whereupon the resulting cellulose acetate solution was deaerated and wet-spun into fibers as described in Example 1.

The cellulose acetate fibers prepared in this manner exhibited the following characteristics:
Degree of esterification: 0.70
Degree of polymerization: 650
Fiber strength, conditioned: 12.9 cN/tex
Fiber elongation, conditioned: 9.3%
Water retentivity: 720%
Synth. urine retentivity: 650%

EXAMPLE 42

16 g (0.1 mol) of cellulose were suspended in 278.4 g (2.81 mol) of 1-methyl-2-pyrrolidone and activated for 30 min. at 155° C. After cooling to 100° C., 29 g (0.68 mol) of LiCl was added. This was followed by cooling to room temperature and overnight stirring. To the clear, viscous solution, 2 g (0.02 mol) of potassium acetate and 12.24 g (0.12 mol) of acetic anhydride were added. To complete the reaction, stirring was continued for 6 hours at 80° C. The reaction mixture was deaerated and spun into fibers as described in Example 1.

The cellulose fibers exhibited the following characteristics:
Degree of esterification: 0.65
Degree of polymerization: 570
Fiber strength, conditioned: 12.2 cN/tex
Fiber elongation, conditioned: 9.5%
Water retentivity: 670%
Synthetic urine retentivity: 645%

EXAMPLE 43

81 g (0.5 mol) of cellulose were suspended in 664.2 g (17.63 mol) of industrial grade dimethylacetamide, activated for 30 minutes at 155° C., cooled to 100° C., and 64.8 g (1.53 mol) of LiCl added thereto. This was followed by cooling to room temperature and overnight stirring.

5 g of potassium acetate (0.05 mol) and 51 g of acetic anhydride (0.5 mol) were added to the clear, very viscous solution and heated for 6 hours at 80° C. The solution was deaerated and spun into fibers as described in Example 1.

The cellulose fibers exhibited the following characteristics:
Degree of esterification: 0.61
Degree of polymerization: 500
Fiber strength, conditioned: 11.8 cN/tex
Fiber elongation, conditioned: 9.1%
Water retentivity: 630%
Synthetic urine retentivity: 570%

The use of higher concentrations of cellulose, such as in Example 43 (10%), is considerably more economical. While the solubility increases with declining degree of polymerization of the cellulose, the fiber strength decreases (at the same degree of stretching), and therefore a compromise between concentration and degree of polymerization is appropriate for the preparation of optimal fibers. Preference is therefore given to the range of concentration between 8 and 12% by weight.

I claim:

1. Fiber insoluble in water and insoluble in 2-methoxyethanol, comprising cellulose acetate, cellulose propionate or cellulose butyrate, having an extremely high absorption capacity for water and physiological liquids, wherein said fiber exhibits:
   a. in the sequence as mentioned above, a degree of esterification of 0.1 to 1.5, 0.1 to 0.95 and 0.15 to 0.8;
   b. an average degree of polymerization of 300 to 700;
   c. a fiber strength in the conditioned state of 6 to 20 cN/tex;
   d. an elongation in the conditioned state of 6 to 20%;
   e. a water retentivity of 200 to 750%; and
   f. a wicking capacity for water of 8 to 18 cm/g of fiber.

2. The fiber of claim 1, wherein said fiber exhibits:
   a. in the sequence as mentioned, a degree of esterification of 0.5 to 0.8, 0.25 to 0.55 and 0.35 to 0.55;
   b. a fiber strength in the conditioned state of 10 to 16 cN/tex;
   c. an elongation in the conditioned state of 8 to 12%; and
   d. a water retentivity of 400 to 720%.

* * * * *